(12) United States Patent
Korth et al.

(10) Patent No.: US 7,339,067 B2
(45) Date of Patent: Mar. 4, 2008

(54) PROCESS FOR PRODUCING MERCAPTOORGANYL (ALKOXYSILANE)

(75) Inventors: Karsten Korth, Grenzach-Wyhlen (DE); Philipp Albert, Lörrach (DE); Dorit Wolf, Oberursel (DE); Steffen Seebald, Kahl am Main (DE); Reimund Pieter, Bensheim (DE); Alfreg Alig, Geiselbach-Omersbach (DE)

(73) Assignee: Evonik Degussa GmbH, Essen (DE)

( * ) Notice: Subject to any disclaimer, the term of this patent is extended or adjusted under 35 U.S.C. 154(b) by 276 days.

(21) Appl. No.: 11/220,835

(22) Filed: Sep. 7, 2005

(65) Prior Publication Data

US 2006/0052621 A1    Mar. 9, 2006

(30) Foreign Application Priority Data

Sep. 7, 2004   (DE) ...................... 10 2004 043 094
May 3, 2005   (DE) ...................... 10 2005 020 536

(51) Int. Cl.
  *C07F 7/08*    (2006.01)
(52) U.S. Cl. ...................... 556/426; 556/627
(58) Field of Classification Search ............... 556/429, 556/427, 627
See application file for complete search history.

(56) References Cited

U.S. PATENT DOCUMENTS

| 5,493,058 A | 2/1996 | Cadot et al. |
| 6,147,242 A | 11/2000 | Batz-Sohn |
| 6,433,206 B1 * | 8/2002 | Gedon et al. ............... 556/427 |
| 6,777,474 B2 * | 8/2004 | Yanagisawa ............... 524/366 |

FOREIGN PATENT DOCUMENTS

EP    1 285 926 A1    2/2003

OTHER PUBLICATIONS

Broadbent, H. Smith et al., "Rhenium Sulfides as Liquid-Phase Hydrogenation Catalysts. A Comparison with Molybdenum Sulfide and Cobalt Polysulfide," Journal of the American Chemical Society, Mar. 20, 1954, pp. 1519-1523, vol. 76, American Chemical Society, Washington, D.C. (XP002227638).
Database Beilstein Online!, Beilstein Institute for Organic Chemistry, Dec. 31, 1996, Frankfurt-Main, Germany (XP002357068).

* cited by examiner

*Primary Examiner*—Yvonne Eyler
*Assistant Examiner*—Yate' K Cutliff
(74) *Attorney, Agent, or Firm*—Robert G. Weilacher; Smith, Gambrell & Russell

(57) ABSTRACT

The invention concerns a process for producing mercaptoorganyl(alkoxysilanes), wherein bis(alkoxysilylorganyl) polysulfides are hydrogenated at temperatures of <190° C. and pressures of <100 bar with hydrogen and a transition metal catalyst without the addition of water, alcohol or $H_2S$.

10 Claims, No Drawings

PROCESS FOR PRODUCING MERCAPTOORGANYL (ALKOXYSILANE)

The invention concerns a process for producing mercaptoorganyl(alkoxysilane).

A process is known from U.S. Pat. No. 6,147,242 for producing 3-mercaptopropyl triethoxysilane by homolytic cleavage of bis(alkoxysilylorganyl)disulfides. In this process the bis(alkoxysilylorganyl)disulfide reacts with an alkali metal and a chlorosilane to give the silylalkyl sulfanyl silane intermediate, which is then converted to the desired mercaptoalkylsilane in the presence of alcohol.

The disadvantages of the process are that an additional reagent (chloroalkylsilane) has to be used and the need to use and dispose of hazardous alkali metal and to isolate the silylalkyl sulfanyl silane intermediate before the alcoholysis step.

Furthermore, a process is known from U.S. Pat. No. 6,433,206 for producing silicon-containing organomercaptans by hydrogenating bis(organylsilyl)polysulfides with group VIII metal catalysts, which have to be protected from toxification with water, $H_2S$ or alcohols.

This process has the disadvantage that at least two additional process steps are necessary (mixing and separating the detoxifying reagent), making the process more energy-intensive and less economical. If alkoxysilanes having long-chain alkoxy substituents (>C8) are used as the starting material, the preparation and separation by distillation, for example, of the alcohols needed as detoxifying reagents becomes increasingly energy-intensive. If alcohols are used as toxification inhibitors which are not the same as the alcohols used for substitution of the alkoxysilanes, interesterifications can occur at the silicon atom of the starting materials used and of the products that are produced. This results in undesired mixed-esterified silane products. From practical and economic viewpoints the addition of detoxifying reagents is therefore limited to alcohols which are already present in the starting material as alkoxy groups. The known process additionally has the disadvantage that only $H_2S$ or water are available as alternatives to the alcohols. $H_2S$ is a highly toxic gas whose use, storage, metering and disposal is very demanding in terms of care, risk preparedness, plant quality and plant safety. The use of water at the same time as alkoxysilanes should be avoided, since it destroys the parent and product compounds under hydrolysis.

The object of the present invention is to provide a process for the reductive cleavage of bis(alkoxysilylorganyl)polysulfides which does not require the use of additional detoxifying reagents such as water, alcohols or hydrogen sulfide for the metal catalysts required and allows a high conversion.

The invention provides a process for producing mercaptoorganyl(alkoxysilane), which is characterised in that bis(alkoxysilylorganyl)polysulfide is hydrogenated at temperatures of <190° C. and pressures <100 bar with hydrogen and a transition metal catalyst without the addition of water, alcohol or $H_2S$.

The reaction can be performed under hydrogenolysis conditions. The transition metal catalyst can be used in catalytically active amounts.

The bis(alkoxysilylorganyl)polysulfide can be a compound having the general formula (I)

$$Z\text{-}A\text{-}S_x\text{-}A\text{-}Z \qquad (I)$$

wherein
x is a number from 1 to 14, by preference 1 to 8, preferably 2 to 4, particularly preferably 2-2.6 and 3.5-3.9,
Z is the same or different and is $SiX^1X^2X^3$ or $Si(OCH_2-CH_2-)_3N$ and
$X^1, X^2, X^3$ can each mutually independently denote hydroxy (—OH),
a linear, branched or cyclic hydrocarbon chain having 1-18 carbon atoms (C1-C18), preferably C1-C10, by preference methyl, ethyl, propyl or butyl,
an alkyl acid substituent $(C_yH_{2y+1})$—C(=O)O— where y=1-25, for example acetoxy $CH_3$—(C=O)O—,
a cycloalkane radical having 5-12 carbon atoms,
a benzyl radical, an alkyl-substituted phenyl radical, alkoxy groups, preferably $(C_1-C_{24})$ alkoxy, with linear or branched hydrocarbon chains, particularly preferably methoxy ($CH_3O$—), ethoxy ($C_2H_5O$—), propoxy ($C_3H_7O$—) or butoxy ($C_4H_9O$—), dodecyloxy ($C_{12}H_{25}O$—), tetradecyloxy ($C_{14}H_{29}O$—), hexadecyloxy ($C_{16}H_{33}O$—) or octadecyloxy ($C_{18}H_{37}O$—),
an alkyl ether group O—$(CR^I_2-CR^I_2)$—O-alk,
an alkyl polyether group O—$(CR^I_2-CR^I_2O)_a$-alk, where a=2-25, preferably a=2-15, particularly preferably a=3-10, most particularly preferably a=3-6, $R^I$ is mutually independently H or an alkyl group, preferably a $CH_3$ group, alk is a linear or branched, saturated or unsaturated alkyl chain having 1-30 carbon atoms (C1-C30), preferably C1-C20, particularly preferably C4-C18, most particularly preferably C8-C16,
a cycloalkoxy group having $(C_5-C_{12})$ atoms,
A is a linear or branched, saturated or unsaturated aliphatic, aromatic or mixed aliphatic/aromatic divalent $C_1-C_{30}$ hydrocarbon chain, preferably $C_1-C_3$, particularly preferably (—$CH_2$—), (—$CH_2$—)$_2$, (—$CH_2$—)$_3$, (—CH($CH_3$)—$CH_2$—) or (—$CH_2$—CH($CH_3$)—).

The bis(alkoxysilylorganyl)polysulfide can be a mixture of compounds having the general formula (I).

Instead of hydrogen substituents, A can be provided with a wide range of substituents, such as e.g. —CN, halogens, for example —Cl, —Br or —F, alcohol functionalities —OH, alkoxides —O-alkyl or —O—(C=O)-alkyl. $CH_2$, $CH_2CH_2$, $CH_2CH_2CH_2$, $CH_2CH(CH_3)$, $CH_2CH_2CH_2CH_2$, $CH_2CH_2CH(CH_3)$, $CH_2CH(CH_3)CH_2$, $CH_2CH_2CH_2CH_2CH_2$, $CH_2CH(CH_3)CH_2CH_2$, $CH_2CH_2CH(CH_3)CH_2$, $CH(CH_3)CH_2CH(CH_3)$ or $CH_2CH(CH_3)CH(CH_3)$ can preferably be used as A.

The group $Z=SiX^1X^2X^3$ can preferably be —$Si(OMe)_3$, —$Si(OEt)_3$, —$SiMe(OMe)_2$, —$SiMe(OEt)_2$), —$SiMe_2(OMe)$, —$SiMe_2(OEt)$, —$Si(OC_{12}H_{25})_3$, $Si(OC_{14}H_{29})_3$, $Si(OC_{16}H_{33})_3$, $Si(OC_{18}H_{37})_3$, $Si(OC_{14}H_{29})_2(OC_{16}H_{33})$, $Si(OC_{14}H_{29})_2(OC_{18}H_{37})$, $Si(OC_{16}H_{33})_2(OC_{14}H_{29})$, $Si(OC_{16}H_{33})_2(OC_{18}H_{37})$, $Si(OC_{18}H_{37})_2(OC_{16}H_{33})$ or $Si(OC_{14}H_{29})(OC_{18}H_{37})_2$.

The following compounds can be used, for example, as the bis(alkoxysilylorganyl)polysulfide having the general formula (I):
$[(MeO)_3Si(CH_2)_3]_2S_2$, $[(MeO)_3Si(CH_2)_3]_2S_3$, $[(MeO)_3Si(CH_2)_3]_2S_4$,
$[(MeO)_3Si(CH_2)_3]_2S_5$, $[(MeO)_3Si(CH_2)_3]_2S_6$, $[(MeO)_3Si(CH_2)_3]_2S_7$,
$[(MeO)_3Si(CH_2)_3]_2S_8$, $[(MeO)_3Si(CH_2)_3]_2S_9$, $[(MeO)_3Si(CH_2)_3]_2S_{10}$,

[(MeO)$_3$Si(CH$_2$)$_3$]$_2$S$_{11}$, [(MeO)$_3$Si(CH$_2$)$_3$]$_2$S$_{12}$, [(EtO)$_3$Si(CH$_2$)$_3$]$_2$S$_2$,
[(EtO)$_3$Si(CH$_2$)$_3$]$_2$S$_3$, [(EtO)$_3$Si(CH$_2$)$_3$]$_2$S$_4$, [(EtO)$_3$Si(CH$_2$)$_3$]$_2$S$_5$,
[(EtO)$_3$Si(CH$_2$)$_3$]$_2$S$_6$, [(EtO)$_3$Si(CH$_2$)$_3$]$_2$S$_7$, [(EtO)$_3$Si(CH$_2$)$_3$]$_2$S$_8$,
[(EtO)$_3$Si(CH$_2$)$_3$]$_2$S$_9$, [(EtO)$_3$Si(CH$_2$)$_3$]$_2$S$_{10}$, [(EtO)$_3$Si(CH$_2$)$_3$]$_2$S$_{11}$,
[(EtO)$_3$Si(CH$_2$)$_3$]$_2$S$_{12}$, [(EtO)$_3$Si(CH$_2$)$_3$]$_2$S$_{13}$, [(EtO)$_3$Si(CH$_2$)$_3$]$_2$S$_{14}$,
[(C$_3$H$_7$O)$_3$Si(CH$_2$)$_3$]$_2$S$_2$, [(C$_3$H$_7$O)$_3$Si(CH$_2$)$_3$]$_2$S$_3$,
[(C$_3$H$_7$O)$_3$Si(CH$_2$)$_3$]$_2$S$_4$, [(C$_3$H$_7$O)$_3$Si(CH$_2$)$_3$]$_2$S$_5$,
[(C$_3$H$_7$O)$_3$Si(CH$_2$)$_3$]$_2$S$_6$, [(C$_3$H$_7$O)$_3$Si(CH$_2$)$_3$]$_2$S$_7$,
[(C$_3$H$_7$O)$_3$Si(CH$_2$)$_3$]$_2$S$_8$, [(C$_3$H$_7$O)$_3$Si(CH$_2$)$_3$]$_2$S$_9$,
[(C$_3$H$_7$O)$_3$Si(CH$_2$)$_3$]$_2$S$_{10}$, [(C$_3$H$_7$O)$_3$Si(CH$_2$)$_3$]$_2$S$_{11}$,
[(C$_3$H$_7$O)$_3$Si(CH$_2$)$_3$]$_2$S$_{12}$, [(C$_3$H$_7$O)$_3$Si(CH$_2$)$_3$]$_2$S$_{13}$,
[(C$_3$H$_7$O)$_3$Si(CH$_2$)$_3$]$_2$S$_{14}$,
[(C$_{12}$H$_{25}$O)(EtO)$_2$Si(CH$_2$)$_3$]S$_x$[(CH$_2$)$_3$Si(OEt)$_3$],
[(C$_{12}$H$_{25}$O)$_2$(EtO)Si(CH$_2$)$_3$]S$_x$[(CH$_2$)$_3$Si(OEt)$_3$],
[(C$_{12}$H$_{25}$O)$_3$Si(CH$_2$)$_3$]S$_x$[(CH$_2$)$_3$Si(OEt)$_3$],
[(C$_{12}$H$_{25}$O)(EtO)$_2$Si(CH$_2$)$_3$]S$_x$[(CH$_2$)$_3$Si(C$_{12}$H$_{25}$O)(OEt)$_2$],
[(C$_{12}$H$_{25}$O)$_2$(EtO)Si(CH$_2$)$_3$]S$_x$[(CH$_2$)$_3$Si (C$_{12}$H$_{25}$O)(OEt)$_2$],
[(C$_{12}$H$_{25}$O)$_3$Si(CH$_2$)$_3$]S$_x$[(CH$_2$)$_3$Si(C$_{12}$H$_{25}$O) (OEt)$_2$],
[(C$_{12}$H$_{25}$O)(EtO)$_2$Si(CH$_2$)$_3$]S$_x$[(CH$_2$)$_3$Si(C$_{12}$H$_{25}$O)$_2$(OEt)],
[(C$_{12}$H$_{25}$O)$_2$(EtO)Si(CH$_2$)$_3$]S$_x$[(CH$_2$)$_3$Si (C$_{12}$H$_{25}$O)$_2$(OEt)],
[(C$_{12}$H$_{25}$O)$_3$Si(CH$_2$)$_3$]S$_x$[(CH$_2$)$_3$Si(C$_{12}$H$_{25}$O)$_2$(OEt)],
[(C$_{12}$H$_{25}$O)(EtO)$_2$Si(CH$_2$)$_3$]S$_x$[(CH$_2$)$_3$Si(C$_{12}$H$_{25}$O)$_3$],
[(C$_{12}$H$_{25}$O)$_2$(EtO)Si(CH$_2$)$_3$]S$_x$[(CH$_2$)$_3$Si (C$_{12}$H$_{25}$O)$_3$],
[(C$_{12}$H$_{25}$O)$_3$Si(CH$_2$)$_3$]S$_x$[(CH$_2$)$_3$Si (C$_{12}$H$_{25}$O)$_3$],
[(C$_{14}$H$_{29}$O)(EtO)$_2$Si(CH$_2$)$_3$]S$_x$[(CH$_2$)$_3$Si(OEt)$_3$],
[(C$_{14}$H$_{29}$O)$_2$(EtO)Si(CH$_2$)$_3$]S$_x$[(CH$_2$)$_3$Si(OEt)$_3$],
[(C$_{14}$H$_{29}$O)$_3$Si(CH$_2$)$_3$]S$_x$[(CH$_2$)$_3$Si(OEt)$_3$],
[(C$_{14}$H$_{29}$O)(EtO)$_2$Si(CH$_2$)$_3$]S$_x$[(CH$_2$)$_3$Si(C$_{14}$H$_{29}$O)(OEt)$_2$],
[(C$_{14}$H$_{29}$O)$_2$(EtO)Si(CH$_2$)$_3$]S$_x$[(CH$_2$)$_3$Si(C$_{14}$H$_{29}$O)(OEt)$_2$],
[(C$_{14}$H$_{29}$O)$_3$Si(CH$_2$)$_3$]S$_x$[(CH$_2$)$_3$Si (C$_{14}$H$_{29}$O) (OEt)$_2$],
[(C$_{14}$H$_{29}$O)(EtO)$_2$Si(CH$_2$)$_3$]S$_x$[(CH$_2$)$_3$Si(C$_{14}$H$_{29}$O)$_2$(OEt)],
[(C$_{14}$H$_{29}$O)$_2$(EtO)Si(CH$_2$)$_3$]S$_x$[(CH$_2$)$_3$Si (C$_{14}$H$_{29}$C)$_2$(OEt)],
[(C$_{14}$H$_{29}$O)$_3$Si(CH$_2$)$_3$]S$_x$[(CH$_2$)$_3$Si (C$_{14}$H$_{29}$O)$_2$(OEt)],
[(C$_{14}$H$_{29}$O)(EtO)$_2$Si(CH$_2$)$_3$]S$_x$[(CH$_2$)$_3$Si(C$_{14}$H$_{29}$O)$_3$],
[(C$_{14}$H$_{29}$O)$_2$(EtO)Si(CH$_2$)$_3$]S$_x$[(CH$_2$)$_3$Si(C$_{14}$H$_{29}$O)$_3$],
[(C$_{14}$H$_{29}$O)$_3$Si(CH$_2$)$_3$]S$_x$[(CH$_2$)$_3$Si(C$_{14}$H$_{29}$O)$_3$],
[(C$_{16}$H$_{33}$O)(EtO)$_2$Si(CH$_2$)$_3$]S$_x$[(CH$_2$)$_3$Si(OEt)$_3$],
[(C$_{16}$H$_{33}$O)$_2$(EtO)Si(CH$_2$)$_3$]S$_x$[(CH$_2$)$_3$Si(OEt)$_3$],
[(C$_{16}$H$_{33}$O)$_3$Si(CH$_2$)$_3$]S$_x$[(CH$_2$)$_3$Si(OEt)$_3$],
[(C$_{16}$H$_{33}$O)(EtO)$_2$Si(CH$_2$)$_3$]S$_x$[(CH$_2$)$_3$Si (C$_{16}$H$_{33}$O) (OEt)$_2$],
[(C$_{16}$H$_{33}$O)$_2$(EtO)Si(CH$_2$)$_3$]S$_x$[(CH$_2$)$_3$Si(C$_{16}$H$_{33}$O)(OEt)$_2$],
[(C$_{16}$H$_{33}$O)$_3$Si(CH$_2$)$_3$]S$_x$[(CH$_2$)$_3$Si (C$_{16}$H$_{33}$O)(OEt)$_2$],
[(C$_{16}$H$_{33}$O)(EtO)$_2$Si(CH$_2$)$_3$]S$_x$[(CH$_2$)$_3$Si(C$_{16}$H$_{33}$O)$_2$(OEt)],
[(C$_{16}$H$_{33}$O)$_2$(EtO)Si(CH$_2$)$_3$]S$_x$[(CH$_2$)$_3$Si(C$_{16}$H$_{33}$O)$_2$(OEt)],
[(C$_{16}$H$_{33}$O)$_3$Si(CH$_2$)$_3$]S$_x$[(CH$_2$)$_3$Si (C$_{16}$H$_{33}$O)$_2$(OEt)],
[(C$_{16}$H$_{33}$O)(EtO)$_2$Si(CH$_2$)$_3$]S$_x$[(CH$_2$)$_3$Si(C$_{16}$H$_{33}$O)$_3$],
[(C$_{16}$H$_{33}$O)$_2$(EtO)Si(CH$_2$)$_3$]S$_x$[(CH$_2$)$_3$Si(C$_{16}$H$_{33}$O)$_3$],
[(C$_{16}$H$_{33}$O)$_3$Si(CH$_2$)$_3$]S$_x$[(CH$_2$)$_3$Si (C$_{16}$H$_{33}$O)$_3$],
[(C$_{18}$H$_{37}$O)(EtO)$_2$Si(CH$_2$)$_3$]S$_x$[(CH$_2$)$_3$Si(OEt)$_3$],
[(C$_{18}$H$_{37}$O)$_2$(EtO)Si(CH$_2$)$_3$]S$_x$[(CH$_2$)$_3$Si(OEt)$_3$],
[(C$_{18}$H$_{37}$O)$_3$Si(CH$_2$)$_3$]S$_x$[(CH$_2$)$_3$Si(OEt)$_3$],
[(C$_{18}$H$_{37}$O)(EtO)$_2$Si(CH$_2$)$_3$]S$_x$[(CH$_2$)$_3$Si (C$_{18}$H$_{37}$O) (OEt)$_2$],
[(C$_{18}$H$_{37}$O)$_2$(EtO)Si(CH$_2$)$_3$]S$_x$[(CH$_2$)$_3$Si (C$_{18}$H$_{37}$O) (OEt)$_2$],
[(C$_{18}$H$_{37}$O)$_3$Si(CH$_2$)$_3$]S$_x$[(CH$_2$)$_3$Si (C$_{18}$H$_{37}$O)(OEt)$_2$],
[(C$_{18}$H$_{37}$O)(EtO)$_2$Si(CH$_2$)$_3$]S$_x$[(CH$_2$)$_3$Si (C$_{18}$H$_{37}$O)$_2$(OEt)],
[(C$_{18}$H$_{37}$O)$_2$(EtO)Si(CH$_2$)$_3$]S$_x$[(CH$_2$)$_3$Si (C$_{18}$H$_{37}$O)$_2$(OEt)],
[(C$_{18}$H$_{37}$O)$_3$Si(CH$_2$)$_3$]S$_x$[(CH$_2$)$_3$Si(C$_{18}$H$_{37}$O)$_2$(OEt)],
[(C$_{18}$H$_{37}$O)(EtO)$_2$Si(CH$_2$)$_3$]S$_x$[(CH$_2$)$_3$Si (C$_{18}$H$_{37}$O)$_3$],
[(C$_{18}$H$_{37}$O)$_2$(EtO)Si(CH$_2$)$_3$]S$_x$[(CH$_2$)$_3$Si (C$_{18}$H$_{37}$O)$_3$] or
[(C$_{18}$H$_{37}$O)$_3$Si(CH$_2$)$_3$]S$_x$[(CH$_2$)$_3$Si (C$_{18}$H$_{37}$O)$_3$].

The bis(alkoxysilylorganyl)polysulfide can be a mixture of various bis(alkoxysilylorganyl)polysulfides having formula I and an average composition of x=1 to 14, preferably x=1 to 8, particularly preferably x=2 to 2.8. A short sulfur chain can be preferable, since it forms less gaseous secondary product in the reaction with H$_2$. Si 266, Si 266/2, Si 261, Si 75 and Si 69 from Degussa AG, Silquest A 1589, Silquest A 1289 or Silquest A 15304 from General Electric-Osi, KBE 846 or KBE 856 from Shin-Etsu Chemical Co. Ltd., Cabrus 4, Cabrus 2A or Cabrus 2B from Daiso Co. Ltd. or HP 669 or HP 1589 from Hung Pai Chemical Company can be used as the bis(alkoxysilylorganyl) polysulfide.

For production reasons the bis(alkoxysilyl)polysulfide can contain 0.01 to 5 wt. % of 3-chloroorganyl(alkoxysilane).

For production reasons the bis(alkoxysilyl)polysulfide can contain 0.001 to 1 wt. % of elemental sulfur.

For production reasons the bis(alkoxysilyl)polysulfide can contain 0.001 to 1 wt. % of alcohol.

The mercaptoorganyl(alkoxysilane) formed can be a compound having the general formula (II)

$$Z\text{-}A\text{-}SH \tag{II}$$

wherein Z and A each mutually independently have the meaning according to formula (I).

The group Z in formula II can preferably be —Si(OMe)$_3$, —Si(OMe)$_2$OH, —Si(OMe) (OH)$_2$, —Si(OEt)$_3$, —Si(OEt)$_2$OH,
—Si(OEt)(OH)$_2$, —SiMe(OMe)$_2$, —SiMe(OEt)$_2$), —SiMe (OH)$_2$,
—SiMe$_2$(OMe), —SiMe$_2$(OEt), —SiMe$_2$(OH), —Si[—O (CO)CH$_3$]$_3$,
—Si(OC$_{12}$H$_{25}$)$_3$, —Si(OC$_{14}$H$_{29}$)$_3$, —Si(OC$_{16}$H$_{33}$)$_3$, —Si (OC$_{18}$H$_{37}$)$_3$,
—Si(OC$_{14}$H$_{29}$)$_2$(OC$_{16}$H$_{33}$), —Si(OC$_{14}$H$_{29}$)$_2$(OC$_{18}$H$_{37}$),
—Si(OC$_{16}$H$_{33}$)$_2$(OC$_{14}$H$_{29}$), —Si(OC$_{16}$H$_{33}$)$_2$(OC$_{18}$H$_{37}$),
—Si(OC$_{18}$H$_{37}$)$_2$(OC$_{16}$H$_{33}$), —Si(OC$_{14}$H$_{29}$)(OC$_{18}$H$_{37}$)$_2$ or
—Si(OCH$_2$—CH$_2$—)$_3$N.

The mercaptoorganyl(alkoxysilane) formed can be a mixture of compounds having the general formula (II).

Mercaptoorganyl(alkoxysilanes) having the general formula (II) can be, for example:
3-mercaptopropyl(trimethoxysilane),
3-mercaptopropyl(dimethoxyhydroxysilane),
3-mercaptopropyl(triethoxysilane),
3-mercaptopropyl(diethoxyhydroxysilane),
3-mercaptopropyl(diethoxymethoxysilane),
3-mercaptopropyl(tripropoxysilane),
3-mercaptopropyl(dipropoxymethoxysilane),
3-mercaptopropyl(dipropoxyhydroxysilane),
3-mercaptopropyl(tridodecanoxysilane),
3-mercaptopropyl(didodecanoxyhydroxysilane),
3-mercaptopropyl(tritetradecanoxysilane),
3-mercaptopropyl(trihexadecanoxysilane),
3-mercaptopropyl(trioctadecanoxysilane),
3-mercaptopropyl(didodecanoxy)tetradecanoxysilane,
3-mercaptopropyl(dodecanoxy)tetradecanoxy(hexadecanoxy) silane,
3-mercaptopropyl(dimethoxymethylsilane),
3-mercaptopropyl(methoxymethylhydroxysilane), 3-mercaptopropyl(methoxydimethylsilane),
3-mercaptopropyl(hydroxydimethylsilane),
3-mercaptopropyl(diethoxymethylsilane),
3-mercaptopropyl(ethoxyhydroxymethylsilane),
3-mercaptopropyl(ethoxydimethylsilane),
3-mercaptopropyl(dipropoxymethylsilane),
3-mercaptopropyl(propoxymethylhydroxysilane),
3-mercaptopropyl(propoxydimethylsilane),
3-mercaptopropyl(diisopropoxymethylsilane),
3-mercaptopropyl(isopropoxydimethylsilane),
3-mercaptopropyl(dibutoxymethylsilane),
3-mercaptopropyl(butoxydimethylsilane),
3-mercaptopropyl(diisobutoxymethylsilane),
3-mercaptopropyl(isobutoxymethylhydroxysilane),
3-mercaptopropyl(isobutoxydimethylsilane),
3-mercaptopropyl(didodecanoxymethylsilane),
3-mercaptopropyl(dodecanoxydimethylsilane),
3-mercaptopropyl(ditetradecanoxymethylsilane),
3-mercaptopropyl(tetradecanoxymethylhydroxysilane),
3-mercaptopropyl(tetradecanoxydimethylsilane),
2-mercaptoethyl(trimethoxysilane),
2-mercaptoethyl(triethoxysilane),
2-mercaptoethyl(diethoxymethoxysilane),
2-mercaptoethyl(tripropoxysilane),
2-mercaptoethyl(dipropoxymethoxysilane),
2-mercaptoethyl(tridodecanoxysilane),
2-mercaptoethyl(tritetradecanoxysilane),
2-mercaptoethyl(trihexadecanoxysilane),
2-mercaptoethyl(trioctadecanoxysilane),
2-mercaptoethyl(didodecanoxy)tetradecanoxysilane,
2-mercaptoethyl(dodecanoxy)tetradecanoxy(hexadecanoxy) silane,
2-mercaptoethyl(dimethoxymethylsilane),
2-mercaptoethyl(methoxymethylhydroxysilane),
2-mercaptoethyl(methoxydimethylsilane),
2-mercaptoethyl(diethoxymethylsilane),
2-mercaptoethyl(ethoxydimethylsilane),
2-mercaptoethyl(hydroxydimethylsilane),
1-mercaptomethyl(trimethoxysilane),
1-mercaptomethyl(triethoxysilane),
1-mercaptomethyl(diethoxymethoxysilane),
1-mercaptomethyl(diethoxyhydroxysilane),
1-mercaptomethyl(dipropoxymethoxysilane),
1-mercaptomethyl(tripropoxysilane),
1-mercaptomethyl(trimethoxysilane),
1-mercaptomethyl(dimethoxymethylsilane),
1-mercaptomethyl(methoxydimethylsilane),
1-mercaptomethyl(diethoxymethylsilane),
1-mercaptomethyl(ethoxymethylhydroxysilane),
1-mercaptomethyl(ethoxydimethylsilane),
3-mercaptobutyl(trimethoxysilane),
3-mercaptobutyl(triethoxysilane),
3-mercaptobutyl(diethoxymethoxysilane),
3-mercaptobutyl(tripropoxysilane),
3-mercaptobutyl(dipropoxymethoxysilane),
3-mercaptobutyl(dimethoxymethylsilane),
3-mercaptobutyl(diethoxymethylsilane),
3-mercaptobutyl(dimethylmethoxysilane),
3-mercaptobutyl(dimethylethoxysilane),
3-mercaptobutyl(dimethylhydroxysilane),
3-mercaptobutyl(tridodecanoxysilane),
3-mercaptobutyl(tritetradecanoxysilane),
3-mercaptobutyl(trihexadecanoxysilane),
3-mercaptobutyl(didodecanoxy)tetradecanoxysilane,
3-mercaptobutyl(dodecanoxy)tetradecanoxy(hexadecanoxy) silane,
3-mercapto-2-methylpropyl(trimethoxysilane),
3-mercapto-2-methylpropyl(triethoxysilane),
3-mercapto-2-methylpropyl(diethoxymethoxysilane),
3-mercapto-2-methylpropyl(tripropoxysilane),
3-mercapto-2-methylpropyl(dipropoxymethoxysilane),
3-mercapto-2-methylpropyl(tridodecanoxysilane),
3-mercapto-2-methylpropyl(tritetradecanoxysilane),
3-mercapto-2-methylpropyl(trihexadecanoxysilane),
3-mercapto-2-methylpropyl(trioctadecanoxysilane),
3-mercapto-2-methylpropyl(didodecanoxy)tetradecanoxysilane,
3-mercapto-2-methylpropyl(dodecanoxy)tetradecanoxy(hexadecanoxy)silane,
3-mercapto-2-methylpropyl(dimethoxymethylsilane),
3-mercapto-2-methylpropyl(methoxydimethylsilane),
3-mercapto-2-methylpropyl(diethoxymethylsilane),
3-mercapto-2-methylpropyl(ethoxydimethylsilane),
3-mercapto-2-methylpropyl(hydroxydimethylsilane),
3-mercapto-2-methylpropyl(dipropoxymethylsilane),
3-mercapto-2-methylpropyl(propoxydimethylsilane),
3-mercapto-2-methylpropyl(diisopropoxymethylsilane),
3-mercapto-2-methylpropyl(isopropoxydimethylsilane),
3-mercapto-2-methylpropyl(dibutoxymethylsilane),
3-mercapto-2-methylpropyl(butoxydimethylsilane),
3-mercapto-2-methylpropyl(diisobutoxymethylsilane),
3-mercapto-2-methylpropyl(isobutoxydimethylsilane),
3-mercapto-2-methylpropyl(didodecanoxymethylsilane),
3-mercapto-2-methylpropyl(dodecanoxydimethylsilane),
3-mercapto-2-methylpropyl(ditetradecanoxymethylsilane) or
3-mercapto-2-methylpropyl(tetradecanoxydimethylsilane).

$[(C_9H_{19}O-(CH_2-CH_2O)_2](MeO)_2Si(CH_2)_3SH$,
$[(C_9H_{19}O-(CH_2-CH_2O)_3](MeO)_2Si(CH_2)_3SH$,
$[(C_9H_{19}O-(CH_2-CH_2O)_4](MeO)_2Si(CH_2)_3SH$,
$[(C_9H_{19}O-(CH_2-CH_2O)_5](MeO)_2Si(CH_2)_3SH$,
$[(C_9H_{19}O-(CH_2-CH_2O)_6](MeO)_2Si(CH_2)_3SH$,
$[(C_{12}H_{25}O-(CH_2-CH_2O)_2](MeO)_2Si(CH_2)_3SH$,
$[(C_{12}H_{25}O-(CH_2-CH_2O)_3](MeO)_2Si(CH_2)_3SH$,
$[(C_{12}H_{25}O-(CH_2-CH_2O)_4](MeO)_2Si(CH_2)_3SH$,
$[(C_{12}H_{25}O-(CH_2-CH_2O)_5](MeO)_2Si(CH_2)_3SH$,
$[(C_{12}H_{25}O-(CH_2-CH_2O)_6](MeO)_2Si(CH_2)_3SH$,
$[(C_{13}H_{27}O-(CH_2-CH_2O)_2](MeO)_2Si(CH_2)_3SH$,
$[(C_{13}H_{27}O-(CH_2-CH_2O)_3](MeO)_2Si(CH_2)_3SH$,
$[(C_{13}H_{27}O-(CH_2-CH_2O)_4](MeO)_2Si(CH_2)_3SH$,
$[(C_{13}H_{27}O-(CH_2-CH_2O)_5](MeO)_2Si(CH_2)_3SH$,
$[(C_{13}H_{27}O-(CH_2-CH_2O)_6](MeO)_2Si(CH_2)_3SH$,
$[(C_{14}H_{29}O-(CH_2-CH_2O)_2](MeO)_2Si(CH_2)_3SH$,
$[(C_{14}H_{29}O-(CH_2-CH_2O)_3](MeO)_2Si(CH_2)_3SH$,
$[(C_{14}H_{29}O-(CH_2-CH_2O)_4](MeO)_2Si(CH_2)_3SH$,
$[(C_{14}H_{29}O-(CH_2-CH_2O)_5](MeO)_2Si(CH_2)_3SH$,
$[(C_{14}H_{29}O-(CH_2-CH_2O)_6](MeO)_2Si(CH_2)_3SH$,
$[(C_9H_{19}O-(CH_2-CH_2O)_2]_2(MeO)Si(CH_2)_3SH$,
$[(C_9H_{19}O-(CH_2-CH_2O)_3]_2(MeO)Si(CH_2)_3SH$,
$[(C_9H_{19}O-(CH_2-CH_2O)_4]_2(MeO)Si(CH_2)_3SH$,
$[(C_9H_{19}O-(CH_2-CH_2O)_5]_2(MeO)Si(CH_2)_3SH$,
$[(C_9H_{19}O-(CH_2-CH_2O)_6]_2(MeO)Si(CH_2)_3SH$,
$[(C_{12}H_{25}O-(CH_2-CH_2O)_2]_2(MeO)Si(CH_2)_3SH$,
$[(C_{12}H_{25}O-(CH_2-CH_2O)_3]_2(MeO)Si(CH_2)_3SH$,
$[(C_{12}H_{25}O-(CH_2-CH_2O)_4]_2(MeO)Si(CH_2)_3SH$,
$[(C_{12}H_{25}O-(CH_2-CH_2O)_5]_2(MeO)Si(CH_2)_3SH$,
$[(C_{12}H_{25}O-(CH_2-CH_2O)_6]_2(MeO)Si(CH_2)_3SH$,
$[(C_{13}H_{27}O-(CH_2-CH_2O)_2]_2(MeO)Si(CH_2)_3SH$,
$[(C_{13}H_{27}O-(CH_2-CH_2O)_3]_2(MeO)Si(CH_2)_3SH$,
$[(C_{13}H_{27}O-(CH_2-CH_2O)_4]_2(MeO)Si(CH_2)_3SH$,
$[(C_{13}H_{27}O-(CH_2-CH_2O)_5]_2(MeO)Si(CH_2)_3SH$,
$[(C_{13}H_{27}O-(CH_2-CH_2O)_6]_2(MeO)Si(CH_2)_3SH$,
$[(C_{14}H_{29}O-(CH_2-CH_2O)_2]_2(MeO)Si(CH_2)_3SH$,
$[(C_{14}H_{29}O-(CH_2-CH_2O)_3]_2(MeO)Si(CH_2)_3SH$,

[(C$_{14}$H$_{29}$O—(CH$_2$—CH$_2$O)$_4$]$_2$(MeO)Si(CH$_2$)$_3$SH,
[(C$_{14}$H$_{29}$O—(CH$_2$—CH$_2$O)$_5$]$_2$(MeO)Si(CH$_2$)$_3$SH,
[(C$_{14}$H$_{29}$O—(CH$_2$—CH$_2$O)$_6$]$_2$(MeO)Si(CH$_2$)$_3$SH,
[(C$_9$H$_{19}$O—(CH$_2$—CH$_2$O)$_2$](EtO)$_2$Si(CH$_2$)$_3$SH,
[(C$_9$H$_{19}$O—(CH$_2$—CH$_2$O)$_3$](EtO)$_2$Si(CH$_2$)$_3$SH,
[(C$_9$H$_{19}$O—(CH$_2$—CH$_2$O)$_4$](EtO)$_2$Si(CH$_2$)$_3$SH,
[(C$_9$H$_{19}$O—(CH$_2$—CH$_2$O)$_5$](EtO)$_2$Si(CH$_2$)$_3$SH,
[(C$_9$H$_{19}$O—(CH$_2$—CH$_2$O)$_6$](EtO)$_2$Si(CH$_2$)$_3$SH,
[(C$_{12}$H$_{25}$O—(CH$_2$—CH$_2$O)$_2$](EtO)$_2$Si(CH$_2$)$_3$SH,
[(C$_{12}$H$_{25}$O—(CH$_2$—CH$_2$O)$_3$](EtO)$_2$Si(CH$_2$)$_3$SH,
[(C$_{12}$H$_{25}$O—(CH$_2$—CH$_2$O)$_4$](EtO)$_2$Si(CH$_2$)$_3$SH,
[(C$_{12}$H$_{25}$O—(CH$_2$—CH$_2$O)$_5$](EtO)$_2$Si(CH$_2$)$_3$SH,
[(C$_{12}$H$_{25}$O—(CH$_2$—CH$_2$O)$_6$](EtO)$_2$Si(CH$_2$)$_3$SH,
[(C$_{13}$H$_{27}$O—(CH$_2$—CH$_2$O)$_2$](EtO)$_2$Si(CH$_2$)$_3$SH,
[(C$_{13}$H$_{27}$O—(CH$_2$—CH$_2$O)$_3$](EtO)$_2$Si(CH$_2$)$_3$SH,
[(C$_{13}$H$_{27}$O—(CH$_2$—CH$_2$O)$_4$](EtO)$_2$Si(CH$_2$)$_3$SH,
[(C$_{13}$H$_{27}$O—(CH$_2$—CH$_2$O)$_5$](EtO)$_2$Si(CH$_2$)$_3$SH,
[(C$_{13}$H$_{27}$O—(CH$_2$—CH$_2$O)$_6$](EtO)$_2$Si(CH$_2$)$_3$SH,
[(C$_{14}$H$_{29}$O—(CH$_2$—CH$_2$O)$_2$](EtO)$_2$Si(CH$_2$)$_3$SH,
[(C$_{14}$H$_{29}$O—(CH$_2$—CH$_2$O)$_3$](EtO)$_2$Si(CH$_2$)$_3$SH,
[(C$_{14}$H$_{29}$O—(CH$_2$—CH$_2$O)$_4$](EtO)$_2$Si(CH$_2$)$_3$SH,
[(C$_{14}$H$_{29}$O—(CH$_2$—CH$_2$O)$_5$](EtO)$_2$Si(CH$_2$)$_3$SH,
[(C$_{14}$H$_{29}$O—(CH$_2$—CH$_2$O)$_6$](EtO)$_2$Si(CH$_2$)$_3$SH,
[(C$_9$H$_{19}$O—(CH$_2$—CH$_2$O)$_2$]$_2$(EtO)Si(CH$_2$)$_3$SH,
[(C$_9$H$_{19}$O—(CH$_2$—CH$_2$O)$_3$]$_2$(EtO)Si(CH$_2$)$_3$SH,
[(C$_9$H$_{19}$O—(CH$_2$—CH$_2$O)$_4$]$_2$(EtO)Si(CH$_2$)$_3$SH,
[(C$_9$H$_{19}$O—(CH$_2$—CH$_2$O)$_5$]$_2$(EtO)Si(CH$_2$)$_3$SH,
[(C$_9$H$_{19}$O—(CH$_2$—CH$_2$O)$_6$]$_2$(EtO)Si(CH$_2$)$_3$SH,
[(C$_{12}$H$_{25}$O—(CH$_2$—CH$_2$O)$_2$]$_2$(EtO)Si(CH$_2$)$_3$SH,
[(C$_{12}$H$_{25}$O—(CH$_2$—CH$_2$O)$_3$]$_2$(EtO)Si(CH$_2$)$_3$SH,
[(C$_{12}$H$_{25}$O—(CH$_2$—CH$_2$O)$_4$]$_2$(EtO)Si(CH$_2$)$_3$SH,
[(C$_{12}$H$_{25}$O—(CH$_2$—CH$_2$O)$_5$]$_2$(EtO) Si(CH$_2$)$_3$SH,
[(C$_{12}$H$_{25}$O—(CH$_2$—CH$_2$O)$_6$]$_2$(EtO)Si(CH$_2$)$_3$SH,
[(C$_{13}$H$_{27}$O—(CH$_2$—CH$_2$O)$_2$]$_2$ (EtO) Si(CH$_2$)$_3$SH,
[(C$_{13}$H$_{27}$O—(CH$_2$—CH$_2$O)$_3$]$_2$ (EtO) Si(CH$_2$)$_3$SH,
[(C$_{13}$H$_{27}$O—(CH$_2$—CH$_2$O)$_4$]$_2$ (EtO) Si(CH$_2$)$_3$SH,
[(C$_{13}$H$_{27}$O—(CH$_2$—CH$_2$O)$_5$]$_2$ (EtO) Si(CH$_2$)$_3$SH,
[(C$_{13}$H$_{27}$O—(CH$_2$—CH$_2$O)$_6$]$_2$ (EtO) Si(CH$_2$)$_3$SH,
[(C$_{14}$H$_{29}$O—(CH$_2$—CH$_2$O)$_2$]$_2$ (EtO) Si(CH$_2$)$_3$SH,
[(C$_{14}$H$_{29}$O—(CH$_2$—CH$_2$O)$_3$]$_2$ (EtO) Si(CH$_2$)$_3$SH,
[(C$_{14}$H$_{29}$O—(CH$_2$—CH$_2$O)$_4$]$_2$ (EtO) Si(CH$_2$)$_3$SH,
[(C$_{14}$H$_{29}$O—(CH$_2$—CH$_2$O)$_5$]$_2$ (EtO) Si(CH$_2$)$_3$SH,
[(C$_{14}$H$_{29}$O—(CH$_2$—CH$_2$O)$_6$]$_2$ (EtO) Si(CH$_2$)$_3$SH,
[(C$_9$H$_{19}$O—(CH$_2$—CH$_2$O)$_2$]$_3$Si(CH$_2$)$_3$SH,
[(C$_9$H$_{19}$O—(CH$_2$—CH$_2$O)$_3$]$_3$Si(CH$_2$)$_3$SH,
[(C$_9$H$_{19}$O—(CH$_2$—CH$_2$O)$_4$]$_3$Si(CH$_2$)$_3$SH,
[(C$_9$H$_{19}$O—(CH$_2$—CH$_2$O)$_5$]$_3$Si(CH$_2$)$_3$SH,
[(C$_9$H$_{19}$O—(CH$_2$—CH$_2$O)$_6$]$_3$Si(CH$_2$)$_3$SH,
[(C$_{12}$H$_{25}$O—(CH$_2$—CH$_2$O)$_2$]$_3$Si(CH$_2$)$_3$SH,
[(C$_{12}$H$_{25}$O—(CH$_2$—CH$_2$O)$_3$]$_3$Si(CH$_2$)$_3$SH,
[(C$_{12}$H$_{25}$O—(CH$_2$—CH$_2$O)$_4$]$_3$Si(CH$_2$)$_3$SH,
[(C$_{12}$H$_{25}$O—(CH$_2$—CH$_2$O)$_5$]$_3$Si(CH$_2$)$_3$SH,
[(C$_{12}$H$_{25}$O—(CH$_2$—CH$_2$O)$_6$]$_3$Si(CH$_2$)$_3$SH,
[(C$_{13}$H$_{27}$O—(CH$_2$—CH$_2$O)$_2$]$_3$Si(CH$_2$)$_3$SH,
[(C$_{13}$H$_{27}$O—(CH$_2$—CH$_2$O)$_3$]$_3$Si(CH$_2$)$_3$SH,
[(C$_{13}$H$_{27}$O—(CH$_2$—CH$_2$O)$_4$]$_3$Si(CH$_2$)$_3$SH,
[(C$_{13}$H$_{27}$O—(CH$_2$—CH$_2$O)$_5$]$_3$Si(CH$_2$)$_3$SH,
[(C$_{13}$H$_{27}$O—(CH$_2$—CH$_2$O)$_6$]$_3$Si(CH$_2$)$_3$SH,
[(C$_{14}$H$_{29}$O—(CH$_2$—CH$_2$O)$_2$]$_3$Si(CH$_2$)$_3$SH,
[(C$_{14}$H$_{29}$O—(CH$_2$—CH$_2$O)$_3$]$_3$Si(CH$_2$)$_3$SH,
[(C$_{14}$H$_{29}$O—(CH$_2$—CH$_2$O)$_4$]$_3$Si(CH$_2$)$_3$SH,
[(C$_{14}$H$_{29}$O—(CH$_2$—CH$_2$O)$_5$]$_3$Si(CH$_2$)$_3$SH,
[(C$_{14}$H$_{29}$O—(CH$_2$—CH$_2$O)$_6$]$_3$Si(CH$_2$)$_3$SH or
HS—CH$_2$—CH$_2$—CH$_2$—Si(OCH$_2$—CH$_2$—)$_3$N.

Hydrogenation can be performed at a hydrogen pressure of 1 to 99 bar, preferably 1 to 80 bar, particularly preferably 1 to 49 bar, most particularly preferably 1 to 35 bar, overpressure.

Hydrogenation can be performed at a temperature of 100 to 185° C., preferably 105 to 175° C., particularly preferably 110 to 165° C., most particularly preferably 120 to 155° C.

The reaction time for the full hydrogenation can be less than 300 min, preferably less than 270 min, particularly preferably less than 240 min, most particularly preferably less than 210 min.

Additives can be added to the reaction mixture before, during or at the end of the reaction.

The additives can bring about a lengthening of the useful life of the catalysts used. The additives can bring about a simpler or improved handling of the catalysts used. The additives can increase the recyclability of the catalysts used. The additives can improve the cost-effectiveness of the process.

Additives can be organosulfur compounds, titanium alkoxylates, amines, organic or inorganic acids or bases or mixtures thereof.

Additives can be carboxylic acids, DMSO, monoalkylamines, dialkylamines or trialkylamines. Additives can be Ti(OC$_4$H$_9$)$_4$ or Ti(OC$_3$H$_7$)$_4$.

The transition metal catalyst can be a catalyst whose catalytically active component consists of nickel, cobalt, rhodium, ruthenium, palladium, iridium or platinum.

The catalytically active component can additionally be doped or can contain additional components, such as e.g. alkali metals, preferably Li, Na, K or Rb, alkaline-earth metals, preferably Be, Mg, Ca, Sr or Ba, elements from the $3^{rd}$ main group, preferably B, Al, Ga or In, elements from the $4^{th}$ main group, preferably C, Si, Ge, Sn or Pb, elements from the $5^{th}$ main group, preferably N, P, As or Sb, elements from the $6^{th}$ main group, preferably O, S, Se or Te, elements from the $7^{th}$ main group, preferably F, Cl, Br or I, or subgroup elements, preferably Sc, Y, Ti, Zr, Hf, V, Nb, Ta, Cr, Mo, W, Mn, Re, Fe, Ru, Co, Rh, Ir, Ni, Pd, Pt, Cu, Ag, Au, Zn or Cd.

The preferred doping component can be a hydride, oxide, halide, for example fluoride, chloride, bromide or iodide, sulfide or nitride.

The doped transition metal catalysts can preferably contain hydrides, oxides, halides, sulfides and/or nitrides of Fe, Ni, Ru, Rh, Pd, Os or Ir as the doping component.

The doped transition metal catalysts can be porous skeleton catalysts of the Raney type, which are doped with transition metals and/or transition metal compounds, for example molybdenum.

The doped transition metal catalysts can be porous, activated metal catalysts of the Raney type, which are doped with transition metals and/or transition metal compounds, for example molybdenum. The doped transition metal catalysts can preferably be activated nickel metal catalysts of the Raney type, which are doped with transition metals and/or transition metal compounds, for example molybdenum.

The proportion by weight of the doping component (in elemental form or as a chemical compound), relative to the weight of the doped transition metal catalysts, can be 0.00001 to 80 wt. %, preferably 0.0001 to 50 wt. %, particularly preferably 0.001 to 15 wt. %, most particularly preferably 0.01 to 7.5 wt. %.

The catalytically active component can be applied to one of the known and conventional catalyst supports, such as e.g. diatomaceous earth, carbon, activated carbon, silica, kieselguhr, alumina or alumosilicate.

The catalytically active component can consist of a finely dispersed, unsupported, activated metal. The activated, unsupported metal can be used as a solid, in suspension or embedded in waxes or oils.

The catalyst concentration relative to the catalytically active metal can be 0.0001 to 1 mmol per 1 g of bis(alkoxysilylorganyl)polysulfide.

With cobalt as the active metal, the catalyst concentration relative to the catalytically active metal can preferably be from 0.001 to 1 mmol, particularly preferably 0.008 to 0.5 mmol, most particularly preferably 0.01 to 0.1 mmol, per 1 g of bis(alkoxysilylorganyl)polysulfide.

With nickel as the active metal, the catalyst concentration relative to the catalytically active metal can preferably be from 0.001 to 1 mmol, particularly preferably 0.01 to 1 mmol, most particularly preferably 0.1 to 0.9 mmol, per 1 g of bis(alkoxysilylorganyl)polysulfide.

With ruthenium as the active metal, the catalyst concentration relative to the catalytically active metal can preferably be from 0.001 to 1 mmol, particularly preferably 0.005 to 0.5 mmol, most particularly preferably 0.005 to 0.3 mmol, per 1 g of bis(alkoxysilylorganyl)polysulfide.

With rhodium as the active metal, the catalyst concentration relative to the catalytically active metal can preferably be from 0.001 to 1 mmol, particularly preferably 0.005 to 0.5 mmol, most particularly preferably 0.005 to 0.1 mmol, per 1 g of bis(alkoxysilylorganyl)polysulfide.

With palladium as the active metal, the catalyst concentration relative to the catalytically active metal can preferably be from 0.001 to 1 mmol, particularly preferably 0.005 to 1 mmol, most particularly preferably 0.05 to 0.3 mmol, per 1 g of bis(alkoxysilylorganyl)polysulfide.

With iridium as the active metal, the catalyst concentration relative to the catalytically active metal can preferably be from 0.001 to 1 mmol, particularly preferably 0.005 to 0.5 mmol, most particularly preferably 0.005 to 0.1 mmol, per 1 g of bis(alkoxysilylorganyl)polysulfide.

With platinum as the active metal, the catalyst concentration relative to the catalytically active metal can preferably be from 0.001 to 1 mmol, particularly preferably 0.005 to 0.5 mmol, most particularly preferably 0.005 to 0.1 mmol, per 1 g of bis(alkoxysilylorganyl)polysulfide.

The conversion which can be expressed quantitatively by the relation "conversion of starting material" per "mmol of catalyst metal" per "minute" can be used as a parameter for comparing the rate of hydrogenolysis at a given temperature T and a constant pressure p.

The conversion can be 0.001 to 10 g of bis(alkoxysilylorganyl)polysulfide per 1 mmol of catalytically active metal per minute. With cobalt as the active metal, the conversion can preferably be 0.001 to 10 g, particularly preferably 0.01 to 10 g, most particularly preferably 0.1 to 5 g, of bis(alkoxysilylorganyl)polysulfide per 1 mmol of catalytically active metal per minute.

With nickel as the active metal, the conversion can preferably be 0.001 to 10 g, particularly preferably 0.01 to 10 g, most particularly preferably 0.1 to 5 g, of bis(alkoxysilylorganyl)polysulfide per 1 mmol of catalytically active metal per minute.

With ruthenium as the active metal, the conversion can preferably be 0.01 to 10 g, particularly preferably 0.1 to 5 g, most particularly preferably 0.2 to 2 g, of bis(alkoxysilylorganyl)polysulfide per 1 mmol of catalytically active metal per minute.

With rhodium as the active metal, the conversion can preferably be 0.001 to 10 g, particularly preferably 0.1 to 5 g, most particularly preferably 0.2 to 3 g, of bis(alkoxysilylorganyl)polysulfide per 1 mmol of catalytically active metal per minute.

With palladium as the active metal, the conversion can preferably be 0.001 to 10 g, particularly preferably 0.11 to 5 g, most particularly preferably 0.15 to 3 g, of bis(alkoxysilylorganyl)polysulfide per 1 mmol of catalytically active metal per minute.

With iridium as the active metal, the conversion can preferably be 0.01 to 10 g, particularly preferably 0.1 to 5 g, most particularly preferably 0.15 to 3 g, of bis(alkoxysilylorganyl)polysulfide per 1 mmol of catalytically active metal per minute.

With platinum as the active metal, the conversion can preferably be 0.01 to 10 g, particularly preferably 0.1 to 5 g, most particularly preferably 0.15 to 3 g, of bis(alkoxysilylorganyl)polysulfide per 1 mmol of catalytically active metal per minute.

The molar conversion which can be expressed quantitatively by the relation "product formed in mmol" per "catalytically active metal" per "minute" can be used as a parameter for comparing the rate of hydrogenolysis at a given temperature T and a constant pressure p.

The molar conversion can be 0.001 to 50 mmol of mercaptoorganyl(alkoxysilane) per 1 mmol of catalytically active metal per minute.

For transition metal catalysts containing iron, nickel, cobalt, ruthenium, rhodium, platinum, iridium or palladium, the molar conversion can preferably be 0.001 to 50 mmol, preferably 0.01 to 40 mmol, particularly preferably 0.05 to 30 mmol, most particularly preferably 0.1 to 20 mmol, of mercaptoorganyl(alkoxysilane) per 1 mmol of group VIII transition metal content per minute.

With the process according to the invention over 90 percent by weight, preferably over 92 percent by weight, particularly preferably over 94 percent by weight, most particularly preferably over 96 percent by weight of the bis(alkoxysilylorganyl)polysulfide used can be converted into a mercaptoorganyl(alkoxysilane). With the process according to the invention the relative proportion (mol %) of the bis(alkoxysilylorganyl)monosulfide content can remain constant.

With the process according to the invention the relative proportion (mol %) of the bis(alkoxysilylorganyl)monosulfide content can increase.

With the process according to the invention the relative proportion (mol %) of the bis(alkoxysilylorganyl)monosulfide content can decrease.

In the process according to the invention the relative proportion of the bis(alkoxysilylorganyl)monosulfide contained in the starting material can be <10 wt. %, preferably <8 wt. %, particularly preferably <6 wt. %, most particularly preferably <4 wt. %.

The process according to the invention can be a batch process or a continuous process.

The batch process can be a slurry process or suspension process, in stirred autoclaves or Buss reactors, for example.

The continuous process can be a slurry process with a continuous liquid and gas supply.

Known reactors for gas/liquid/solid reactions can be used in the continuous process. Typical representatives for fixedbed reactors are the trickle-bed and liquid-phase reactor, for suspension reactors the stirred-tank reactor, bubble column and fluidised bed.

any further detail containing primarily bis(3-triethoxysilylpropyl)disulfide is used as the polysulfane silane. No mention is made of secondary product formation or similar.

TABLE 1

| No | Conditions | | | Catalyst | Material ratios | | | Time | Product composition | | | | Conversion Amount of converted silane to catalyst metal per minute g/mmol/min | Mass balance Total silane product wt. % |
| | Temperature °C. | Pressure psig | Pressure bar | | Amount of cat. g | Amount of metal on catalyst g | Amount of molar metal on catalyst mmol | Amount of polysulfane silane g | Time min | SH wt. % | S1 wt. % | S2 wt. % | Sx wt. % | | |
|---|---|---|---|---|---|---|---|---|---|---|---|---|---|---|---|
| 1 | 190 | 620 | 104.16 | 55% Ni on kieselguhr | 2 | 1.1 | 18.7 | 591.4 | 60 | 11.2 | 9.5 | 69.4 | 7.3 | 0.059 | 97.4 |
|   |     |     |        |                       |   |     |      |       | 120 | 18.4 | 9 | 63 | 7.2 | 0.048 | 97.6 |
|   |     |     |        |                       |   |     |      |       | 180 | 30.7 | 8.5 | 52.6 | 5 | 0.054 | 96.8 |
| 5 | 190 | 600 | 100.8  | 55% Ni on kieselguhr | 5 | 2.75 | 46.9 | 502 | 60 | 13.6 | 8.9 | 62.5 | 7.3 | 0.024 | 92.3 |
|   |     |     |        |                       |   |     |      |     | 120 | 30.7 | 7.8 | 49.8 | 3 | 0.027 | 91.3 |
|   |     |     |        |                       |   |     |      |     | 1800 | 44 | 7.5 | 36.2 | 0 | 0.026 | 87.7 |
| 6 | 200 | 600 | 100.8  | 55% Ni on kieselguhr | 5 | 2.75 | 46.9 | 490 | 60 | 18.2 | 8.4 | 62 | 5.7 | 0.032 | 94.3 |
|   |     |     |        |                       |   |     |      |     | 120 | 39 | 8 | 45.9 | 1.6 | 0.034 | 94.5 |
|   |     |     |        |                       |   |     |      |     | 1800 | 57 | 7.88 | 28.7 | 0 | 0.033 | 93.6 |
| 3 | 190 | 300 | 50.4   | 55% Ni on kieselguhr | 5 | 2.75 | 46.9 | 547 | 60 | 10.8 | 8.33 | 65.4 | 9.7 | 0.021 | 94.2 |
|   |     |     |        |                       |   |     |      |     | 120 | 39.1 | 7.94 | 44.9 | 1.6 | 0.038 | 93.5 |
| 4 | 190 | 1000 | 168   | 55% Ni on kieselguhr | 5 | 2.75 | 46.9 | 503 | 0 | 0 | | | | | |
|   |     |     |        |                       |   |     |      |     | 60 | 17.8 | 8.69 | 60.2 | 8 | 0.032 | 94.7 |
|   |     |     |        |                       |   |     |      |     | 120 | 66.5 | 7.9 | 20.7 | 0 | 0.059 | 95.1 |
| 2 | 100 | 1400 | 235.2 | 5% Pd/C | 4 | 0.2 | 1.9 | 637 | 60 | 1.9 | 9.8 | 89.1 | 1.2 | 0.107 | 102.0 |

Despite the gentler, less resource-intensive reaction conditions, the conversions for <100 bar are better than or at least the same as the conversions previously known from the prior art.

The omission of detoxifying reagents, such as water, alcohol and H₂S, has not been shown to have a negative impact on hydrogenation.

In the process according to the invention a higher activity in comparison to the known catalysts can be achieved with relatively gentle conditions. Conversions of up to 0.42 g of bis(alkoxysilylorganyl)polysulfide can be obtained per mmol of catalyst metal per minute. Surprisingly, these high conversions can be achieved even with relatively gentle reaction conditions in terms of temperature and pressure. A higher conversion not only improves the space-time yield considerably, but also reduces the specific energy consumption for the production of mercaptoorganyl(alkoxysilanes) by reductive cleavage with H₂ from bis(alkoxysilylorganyl) polysulfides. A lower energy consumption and gentler reaction conditions place the plant under less stress, resulting among other things in reduced wear. A lower energy consumption in the production of mercaptoorganyl(alkoxysilanes) improves the energy balance for the process and reduces environmental pollution.

EXAMPLES

Table 1 shows the comparative examples from U.S. Pat. No. 6,433,206. A disulfane silane mixture not specified in Tables 2 and 3 show the examples according to the invention on the basis of a disulfane silane. In an apparatus supplied by Chemscan, consisting of 8 parallel oil bath-heated autoclaves having reactor volumes of 20 ml and equipped with anchor-shaped magnetic stirrers, which rotate on a fixed shaft in the centre of the reactor at a speed of 1300 rpm, Si 266 (commercial product from Degussa AG/[bis (alkoxysilylorganyl)disulfide]) is hydrogenated catalytically in accordance with the conditions in Table 2 and 3. The reaction is ended after the specified times.

In the "Product composition" columns in Table 2 and 3 only the components mercaptopropyl(triethoxysilane), bis(triethoxysilylpropyl)disulfide, bis(triethoxysilylpropyl) trisulfide and bis(triethoxysilylpropyl)tetrasulfide are taken into account. Bis(triethoxysilylpropyl)monosulfide and 3-chloropropyl(triethoxysilane) are disregarded.

The stated product composition is determined by $^1$H-NMR.

According to combined GC/HPLC and NMR analyses, the Si 266 used for the experiments contained 1.7 wt. % bis(triethoxysilylpropyl)monosulfide, 84 wt. % bis(triethoxysilylpropyl)disulfide, 12 wt. % bis(triethoxysilylpropyl)trisulfide and 1 wt. % bis(triethoxysilylpropyl)tetrasulfide.

The average chain length determined for the polysulfane mixture is approximately 2.14 (only the average from S2-S10 is taken into account). The Si 266 used contains 0.8 wt. % of 3-chloropropyl(triethoxysilane).

TABLE 2

| Ex. | Temperature °C | Pressure bar | Catalyst type | Amount of catalyst mg | Amount of metal rel. to catalyst mg | Amount of metal rel. to catalyst mmol | Amount of silane Si 266 g | Time React. time min | SH wt. % | S2 wt. % | S3 wt. % | S4 wt. % | Conversion Amount of converted silane to amount of catalyst metal per minute g/mmol/min |
|---|---|---|---|---|---|---|---|---|---|---|---|---|---|
| 1 | 175 | 50 | CE 105R/W 5% Pd + 0.5% Mo | 100.1 | 5.005 | 0.0470 | 6 | 594 | 86 | 14 | 0 | 0 | 0.184 |
| 2 | 152 | 50 | H 105 BA/W 5% Ru | 79.70 | 3.99 | 0.0374 | 6 | 350 | 53 | 47 | 0 | 0 | 0.242 |
| 3 | 162 | 50 | H 105 BA/W 5% Ru | 100.6 | 5.03 | 0.0498 | 6 | 292 | 62 | 38 | 0 | 0 | 0.256 |
| 4 | 174 | 50 | H 105 BA/W 5% Ru | 100.2 | 5.01 | 0.0496 | 6 | 430 | 100 | 0 | 0 | 0 | 0.281 |
| 5 | 168 | 50 | H 105 BA/W 5% Ru | 50.5 | 2.525 | 0.0250 | 6 | 453 | 60 | 40 | 0 | 0 | 0.316 |
| 6 | 164 | 95 | H 105 BA/W 5% Ru | 101.1 | 5.055 | 0.0500 | 6 | 400 | 100 | 0 | 0 | 0 | 0.300 |
| 7 | 175 | 95 | H 105 BA/W 5% Ru | 53.3 | 2.665 | 0.0264 | 6 | 400 | 73 | 27 | 0 | 0 | 0.416 |
| 8 | 124 | 10 | E105Y/W 5% Pd | 20.00 | 1.00 | 0.0094 | 6 | 80 | 3.10 | 85.10 | 11.90 | 0 | 0.247 |

TABLE 3

| No. | T °C | p bar | Catalyst type | Amount of catalyst mg | Amount of metal rel. to catalyst mg | Amount of metal rel. to catalyst mmol | Amount of silane Si 266 g | Reaction time min | SH wt. % | S2 wt. % | S3 wt. % | S4 wt. % | Conversion Amount of converted silane to amount of catalyst g/mmol/min |
|---|---|---|---|---|---|---|---|---|---|---|---|---|---|
| 9 | 141 | 51 | B 111 W | 50 | 50 | 0.852 | 6 | 252 | 100.0 | 0.0 | 0.0 | 0.0 | 0.028 |
| 10 | 143 | 55 | G-96 B/66 wt. % Ni + alkaline promoters | 50 | 27.5 | 0.562 | 6 | 280 | 100.0 | 0.0 | 0.0 | 0.0 | 0.038 |
| 11 | 137 | 53 | T-8027/52 wt. % Ni + 2 wt. % Zr | 50 | 26 | 0.443 | 6 | 287 | 100.0 | 0.0 | 0.0 | 0.0 | 0.047 |

Table 4 shows the examples according to the invention on the basis of a tetrasulfane silane. In an apparatus supplied by Chemscan, consisting of 8 parallel oil bath-heated autoclaves having reactor volumes of 20 ml and equipped with anchor-shaped magnetic stirrers, which rotate on a fixed shaft in the centre of the reactor at a speed of 1300 rpm, Si 69 (commercial product from Degussa AG/[bis(alkoxysilylorganyl)tetrasulfide]) is hydrogenated catalytically in accordance with the conditions in Table 4.

The reaction is ended after the specified times.

In the "Product composition" columns in Table 4 only the components mercaptopropyl(triethoxysilane), bis(triethoxysilylpropyl)disulfide, bis(triethoxysilylpropyl)trisulfide and bis(triethoxysilylpropyl)tetrasulfide are taken into account. Bis(triethoxysilylpropyl)monosulfide and 3-chloropropyl(triethoxysilane) are disregarded.

The stated product composition is determined by $^1$H-NMR.

According to combined GC/HPLC and NMR analyses, the Si 69 used for the experiments contains
0.1 wt. % bis(triethoxysilylpropyl)monosulfide,
17 wt. % bis(triethoxysilylpropyl)disulfide,
27 wt. % bis(triethoxysilylpropyl)trisulfide,
25 wt. % bis(triethoxysilylpropyl)tetrasulfide and approx. 29 wt. % bis(triethoxysilylpropyl)polysulfide with -Sx- x≧5.

The average chain length determined for the polysulfane mixture is 3.75. The Si 69 contains 1.4 wt. % of 3-chloropropyl(triethoxysilane).

TABLE 4

| Example no. | Temperature °C | Pressure bar | Catalyst type | Amount of cat. mg | Amount of metal rel. to catalyst mg | Amount of metal rel. to catalyst mmol | Amount of silane Si 69 g | Reaction time min | SH wt. % | S2 wt. % | S3 wt. % | S4 wt. % | Conversion Amount of converted silane to amount of catalyst metal per minute g/mmol/min |
|---|---|---|---|---|---|---|---|---|---|---|---|---|---|
| 12 | 173 | 62.5 | H 105 BA/W 5% Ru | 50.6 | 2.5 | 0.025 | 6.6 | 400 | 9.9 | 22.0 | 27.1 | 16.9 | 0.066 |

TABLE 4-continued

| | Parameter | | | Material ratios | | | | | Product composition | | | | Conversion Amount of converted silane to amount of catalyst metal per minute g/mmol/min |
|---|---|---|---|---|---|---|---|---|---|---|---|---|---|
| Example no. | Temperature °C. | Pressure bar | Catalyst type | Amount of cat. mg | Amount of metal rel. to catalyst mg | Amount of metal rel. to catalyst mmol | Amount of silane Si 69 g | Reaction time min | SH wt. % | S2 wt. % | S3 wt. % | S4 wt. % | |
| 13 | 172 | 89.0 | H 105 BA/ W 5% Ru | 50.6 | 2.5 | 0.025 | 6.6 | 410 | 11.1 | 22.3 | 25.5 | 20.3 | 0.071 |

The meanings of the abbreviations contained in the tables are as follows:
SH=3-mercaptopropyl(triethoxysilane),
S2=bis(triethoxysilylpropyl)disulfide,
S3=bis(triethoxysilylpropyl)trisulfide,
S4=bis(triethoxysilylpropyl)tetrasulfide.
Si 69 [bis(alkoxysilylorganyl)tetrasulfide] and Si 266 [bis(alkoxysilylorganyl)disulfide] are commercial bis(alkoxysilylorganyl)polysulfides from Degussa AG.

The catalysts with the abbreviated names H 105 BA/W 5% Ru, E 105 RS/W 5% Pd, CE 105 R/W 5% Pd+0.5% Mo, E 105 Y/W 5% Pd, and B 111 W are obtained from Degussa AG.

The catalysts with the abbreviated names H 105 BA/W 5% Ru, E 105 RS/W 5% Pd, CE 105 R/W 5% Pd+0.5% Mo and E 105 Y/W 5% Pd are noble metal powder catalysts which are produced by applying a noble metal component such as ruthenium or palladium to a porous support having a large surface area. The proportion of the noble metal component here is 5 wt. % relative to the dry weight of the catalyst. The catalysts are used as powdered, free-flowing solids. The cited catalysts are supported on activated carbons.

The catalyst with the abbreviated name B 111 W was an activated metal catalyst produced by suspending finely dispersed elemental nickel in an aqueous solution. After separating off the metal component the catalyst is used as a powdered solid.

The catalysts G-96 B and T 8027 are commercial products from Süd-Chemie AG.

The catalyst G-96 B contains 66% nickel and alkaline promoters.

The catalyst T 8027 contains 52% nickel and 2.4% zirconium.

For analysis of the products a Bruker DRX 500 NMR instrument is used inter alia, in accordance with the rules and operating instructions known to the person skilled in the art. The measuring frequencies are 99.35 MHz for $^{29}$Si nuclei and 500.13 MHz for $^1$H nuclei. Tetramethylsilane (TMS) is used as a control.

The analysis of bis(alkoxysilylorganyl)polysulfides and mercaptoorganyl(alkoxysilanes) and mixtures thereof can be carried out with GC, HPLC and NMR (U. Görl, J. Münzenberg, D. Luginsland, A. Müller Kautschuk Gummi Kunststoffe 1999, 52(9), 588, D. Luginsland Kautschuk Gummi Kunststoffe 2000, 53(1-2), 10 or M. W. Backer et al, *Polymer Preprints* 2003, 44(1), 245)

In the case of nickel at 190-200° C. and <100 bar, for a disulfane silane not specified in any further detail, the comparative examples from U.S. Pat. No. 6,433,206 without addition of detoxifying reagents yield conversions of only 0.021-0.038 g/mmol/min.

In the case of palladium at 190-200° C. and 235 bar, for a disulfane silane not specified in any further detail, the comparative example from U.S. Pat. No. 6,433,206 without addition of detoxifying reagents yields a conversion of 0.107 g/mmol/min.

The process according to the invention with the catalysts based on ruthenium achieves a conversion of 0.42 g/mmol/min under relatively gentle conditions in terms of temperature and pressure (a maximum of 175° C. at a maximum of 95 bar). The process according to the invention with catalysts based on doped nickel achieves a conversion of 0.38-0.47 g/mmol/min under relatively gentle conditions in terms of temperature and pressure (a maximum of 143° C. at a maximum of 55 bar). The process according to the invention with catalysts based on doped palladium achieves a conversion of 0.184 g/mmol/min under relatively gentle conditions in terms of temperature and pressure (175° C. at a maximum of 50 bar).

The process according to the invention with catalysts based on palladium achieves a conversion of 0.247 g/mmol/min under relatively gentle conditions in terms of temperature and pressure (124° C. at a maximum of 10 bar).

The invention claimed is:

1. Process for producing mercaptoorganyl(alkoxysilanes), characterised in that bis(alkoxysilylorganyl) polysulfides are hydrogenated at temperatures of <190° C. and pressures of <100 bar with hydrogen and a transition metal catalyst without the addition of water, alcohol or $H_2S$.

2. Process for producing mercaptoorganyl(alkoxysilanes) according to claim 1, characterised in that the bis(alkoxysilylorganyl)polysulfide is a compound having the general formula (I)

$$Z\text{-}A\text{-}S_x\text{-}A\text{-}Z \tag{I}$$

wherein
x is a number from 1 to 14,
Z is the same or different and is $SiX^1X^2X^3$ or $Si(OCH_2\text{---}CH_2\text{---})_3N$ and
$X^1$, $X^2$, $X^3$ can each mutually independently denote hydroxy (—OH),
a linear, branched or cyclic hydrocarbon chain having 1-18 carbon atoms (C1-C18),
an alkyl acid substituent $(C_yH_{2y+1})$—C(═O)O— where y=1-25, a substituted alkyl acid or alkenyl acid substituent,
a cycloalkane radical having 5-12 carbon atoms,
a benzyl radical, an alkyl-substituted phenyl radical, alkoxy groups with linear or branched hydrocarbon chains,
an alkyl ether group O—(CR$^I_2$—CR$^I_2$)—O-alk,
an alkyl polyether group O—(CR$^I_2$—CR$^I_2$O)$_a$-alk, where a=2-25, R$^I$ is mutually independently H or an alkyl group, alk is a linear or branched, saturated or unsaturated alkyl chain having 1-30 carbon atoms (C1-C30),
a cycloalkoxy group having (C$_5$-C$_{12}$) atoms,
A is a linear or branched, saturated or unsaturated aliphatic, aromatic or mixed aliphatic/aromatic divalent C$_1$-C$_{30}$ hydrocarbon chain.

3. Process for producing mercaptoorganyl(alkoxysilanes) according to claim 2, characterised in that the bis(alkoxysilylorganyl)polysulfides are mixtures of compounds having the general formula I.

4. Process for producing mercaptoorganyl(alkoxysilanes) according to claim 1, characterised in that the catalytically active component is additionally doped or contains additional components.

5. Process for producing mercaptoorganyl(alkoxysilanes) according to claim 4, characterised in that the catalytically active component contains one or more alkali metals, alkaline-earth metals, elements from the 3$^{rd}$ main group, elements from the 4$^{th}$ main group, elements from the 5$^{th}$ main group, elements from the 6$^{th}$ main group, elements from the 7$^{th}$ main group or subgroup elements.

6. Process for producing mercaptoorganyl(alkoxysilanes) according to claim 1, characterised in that the transition metal catalyst contains nickel, cobalt, rhodium, ruthenium, palladium, iridium or platinum as the catalytically active component.

7. Process for producing mercaptoorganyl(alkoxysilanes) according to claim 1, characterised in that the catalyst concentration, relative to the catalytically active metal, is 0.0001 to 1 mmol per 1 g of bis(alkoxysilylorganyl)polysulfide.

8. Process for producing mercaptoorganyl(alkoxysilanes) according to claim 1, characterised in that the process is performed batchwise.

9. Process for producing mercaptoorganyl(alkoxysilanes) according to claim 1, characterised in that the process is performed continuously.

10. Process for producing mercaptoorganyl(alkoxysilanes) according to claim 1, characterised in that the reaction mixture contains additives.

* * * * *